US010039575B2

(12) United States Patent
Fortin et al.

(10) Patent No.: US 10,039,575 B2
(45) Date of Patent: Aug. 7, 2018

(54) DYNAMIC INTERVERTEBRAL STABILISATION DEVICE

(71) Applicant: COUSIN BIOTECH SAS, Wervicq Sud (FR)

(72) Inventors: Frederic Fortin, Pessac (FR); Johann Robin, Begles (FR); Brice Sennequier, Pessac (FR)

(73) Assignee: COUSIN BIOTECH SAS, Wervicq Sud (FR)

( * ) Notice: Subject to any disclaimer, the term of this patent is extended or adjusted under 35 U.S.C. 154(b) by 0 days.

(21) Appl. No.: 14/902,732

(22) PCT Filed: Jul. 1, 2013

(86) PCT No.: PCT/FR2013/000167
§ 371 (c)(1),
(2) Date: Apr. 20, 2016

(87) PCT Pub. No.: WO2015/001197
PCT Pub. Date: Jan. 8, 2015

(65) Prior Publication Data
US 2016/0220285 A1 Aug. 4, 2016

(51) Int. Cl.
*A61B 17/70* (2006.01)
*A61F 2/44* (2006.01)
(Continued)

(52) U.S. Cl.
CPC ...... *A61B 17/7062* (2013.01); *A61B 17/7055* (2013.01); *A61B 17/7071* (2013.01);
(Continued)

(58) Field of Classification Search
CPC .................. A61B 17/7062; A61B 2017/567
See application file for complete search history.

(56) References Cited

U.S. PATENT DOCUMENTS 6,733,532 B1 * 5/2004 Gauchet .................. A61F 2/442
606/247
7,326,250 B2 * 2/2008 Beaurain ............... A61F 2/4425
606/86 A
(Continued)

FOREIGN PATENT DOCUMENTS

FR 2 787 017 A1 6/2000
FR 2 902 639 A1 12/2007
(Continued)

OTHER PUBLICATIONS

International Search Report dated Apr. 22, 2014 in PCT/FR2013/000167 filed Jul. 1, 2013.

*Primary Examiner* — Ellen C Hammond
*Assistant Examiner* — Stuart S Bray
(74) *Attorney, Agent, or Firm* — Oblon, McClelland, Maier & Neustadt, L.L.P.

(57) ABSTRACT

A dynamic intervertebral stabilization device (1) comprising the following elements:
an upper hook (10),
a lower hook (13),
a hollow cylindrical body (14),
a viscoelastic element,
as well as an upper hook (10) integrating a piston (11), which is braced with a minimum of contact on the viscoelastic element, which permits upper (10) and lower (13) hooks to be moved in multiaxial manner within a solid angle ($\Omega$) while absorbing deformations in compression and in flexion by virtue of the damping produced by the viscoelastic element.

15 Claims, 9 Drawing Sheets

Figure 1:
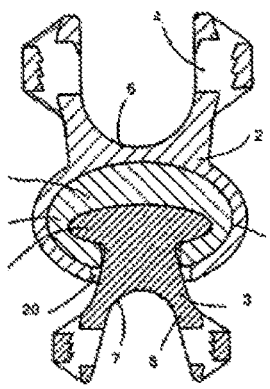

(51) Int. Cl.
*A61F 2/30* (2006.01)
*A61B 17/56* (2006.01)

(52) U.S. Cl.
CPC ...... *A61F 2/4405* (2013.01); *A61B 2017/567* (2013.01); *A61F 2002/30563* (2013.01)

(56) References Cited

U.S. PATENT DOCUMENTS

| | | | | |
|---|---|---|---|---|
| 7,959,678 | B2* | 6/2011 | Filippi | A61F 2/4425 623/17.14 |
| 8,002,834 | B2* | 8/2011 | de Villiers | A61F 2/4425 623/17.14 |
| 8,092,538 | B2* | 1/2012 | de Villiers | A61F 2/4425 623/17.14 |
| 8,226,724 | B2* | 7/2012 | Doty | A61F 2/4425 623/17.11 |
| 8,287,598 | B1* | 10/2012 | Doty | A61F 2/4425 623/17.16 |
| 8,377,138 | B2* | 2/2013 | Reo | A61F 2/442 623/17.13 |
| 8,535,379 | B2* | 9/2013 | Moskowitz | A61F 2/4425 623/17.15 |
| 8,764,833 | B2* | 7/2014 | de Villiers | A61F 2/30771 623/17.11 |
| 8,808,381 | B2* | 8/2014 | Kim | A61F 2/442 623/17.13 |
| 8,906,096 | B2* | 12/2014 | Hewko | A61F 2/4425 623/17.16 |
| 8,911,498 | B2* | 12/2014 | Bartish, Jr. | A61F 2/442 623/17.14 |
| 9,011,542 | B2* | 4/2015 | Lee | A61B 17/1659 623/17.15 |
| 9,011,544 | B2* | 4/2015 | Arramon | A61F 2/4425 623/17.11 |
| 9,044,278 | B2* | 6/2015 | Tanaka | A61B 17/7062 |
| 9,220,603 | B2* | 12/2015 | Arramon | A61F 2/4425 |
| 9,265,618 | B2* | 2/2016 | Rashbaum | A61F 2/4425 |
| 9,289,310 | B2* | 3/2016 | Chaput | A61B 17/686 |
| 9,345,583 | B2* | 5/2016 | Josse | A61F 2/4425 |
| 9,358,121 | B2* | 6/2016 | Chaput | A61F 2/4425 |
| 9,655,741 | B2* | 5/2017 | de Villiers | A61F 2/4425 |
| 2004/0106995 | A1* | 6/2004 | Le Couedic | A61B 17/7062 623/17.11 |
| 2004/0220568 | A1* | 11/2004 | Zucherman | A61B 17/7025 606/279 |
| 2006/0106381 | A1* | 5/2006 | Ferree | A61F 2/4455 606/248 |
| 2010/0121381 | A1* | 5/2010 | Berta | A61B 17/7055 606/264 |
| 2010/0204732 | A1* | 8/2010 | Aschmann | A61B 17/7062 606/249 |
| 2011/0152935 | A1* | 6/2011 | Fortin | A61B 17/7023 606/257 |
| 2011/0264216 | A1* | 10/2011 | Makower | A61B 17/68 623/13.12 |
| 2013/0304208 | A1* | 11/2013 | Clifford | A61B 17/56 623/13.12 |
| 2014/0277445 | A1* | 9/2014 | Slone | A61B 17/56 623/13.12 |
| 2014/0277446 | A1* | 9/2014 | Clifford | A61B 17/56 623/13.12 |

FOREIGN PATENT DOCUMENTS

| | | |
|---|---|---|
| FR | 2 931 354 A1 | 11/2009 |
| FR | 2 951 630 A1 | 4/2011 |
| FR | 2 957 516 A1 | 9/2011 |

* cited by examiner

DYNAMIC INTERVERTEBRAL STABILISATION DEVICE

FIELD OF THE INVENTION

The invention relates to a dynamic interspinous or interlaminar stabilization device, which works in multiaxial manner while at the same time damping the applied mechanical stresses. This device offers multiple functions and more numerous advantages, in particular a better useful life, than those of the prior art, which we shall now examine in detail.

PRIOR ART

Four prior art documents will be examined:

The first document is a French Patent published under number FR2884136, which describes a surgical implant assisting the movements of two successive vertebrae and which comprises (see FIG. 1 of the prior art) upper and lower pieces 2 and 3 assembled together by means of reciprocal associating means 16, which function as a ball joint, composed of a lodging 17 receiving a protuberance 18 of ovoidal shape, surrounded by a viscoelastic means 19, which absorbs the shocks. Such an assembly between pieces of very different rigidity with shapes close to that of an egg has abrupt changes of radii of curvature. This will generate interfaces where different materials are joined mechanically to one another. These latter will deform in very different manner and create assembly prestresses, with large zones of contact, which induce considerable friction effects and therefore accelerated aging of the device 1. In addition, in this concept, viscoelastic means 19 is open to the exterior biological medium, which is potentially very aggressive toward the viscoelastic materials, which will add a supplementary acceleration to aging by phenomena of oxidation, calcification and hydrolysis.

A second document, French Patent FR2915367, describes an invention (see FIGS. 2 and 3) composed of an upper piece 2 and lower piece 3, each comprising rigid connecting elements 20 and viscoelastic connecting elements 30, which form a pivot joint. These means are assembled together by pins 51, which are disposed to pass transversely through them, thus greatly weakening them, especially with regard to viscoelastic element 30, which will be deformed with the presence of orifices 50, which constitute starting points for rupture when device 1 is subjected to mechanical forces.

A third document, French Patent FR2951630, describes an invention that does not have a damping function as performing as the present invention. In addition, the clearances adopted in this prior art invention are different from the spaces created by radii R1 and R2 of the central cavity, which contains the viscoelastic element in which this latter can be deformed with less friction. In the present invention it is possible to damp the mechanical stresses in tension, whereas this was impossible with the prior art invention.

A fourth document, US Patent 20070233096, describes a device that suggests only a difference of curvature between two surfaces and this graphic suggestion being insufficiently described to lead to the present invention.

The present invention describes and claims new elements, pieces, materials and conception, forming means that will lead to definition of a new device. These are:
- a central viscoelastic element and the components that surround it,
- new pieces that the prior art devices do not have. They are easier to produce and assemble, while being more resistant to the stresses imposed in the environment of the spine. The shapes of the upper and lower hooks were specifically designed to interlock easily between the vertebrae and to overlap with one another. The entirety of these new means will permit the present invention to have new applications, especially the possibilities of tilting and multiaxial rotation, and this independently of any aspect of damping, which is essential. The rotational movements will be possible independently of the movements of compression and of those related to the damping of the device, which functions are impossible to achieve with the aforesaid prior art inventions.

The figures provided for understanding the invention are:

FIG. 1, plate 1/9, sectional view of the device corresponding to French Patent 2884136 (prior art)

Figure 2:
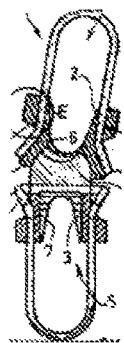

FIG. 2, plate 1/9, sectional view of the device corresponding to French Patent 2915367 (prior art)

Figure 3:
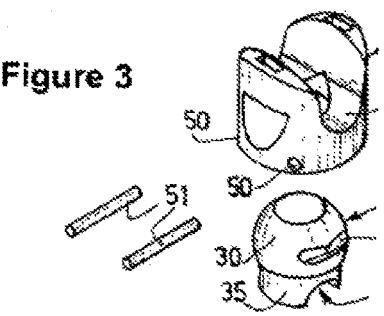

FIG. 3, plate 1/9, perspective view of the device corresponding to French Patent 2915367 (prior art)

Figure 4:
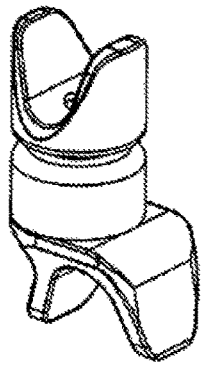

FIG. 4, plate 1/9, perspective view of the device corresponding to French Patent 2951630 (prior art)

Figure 5:
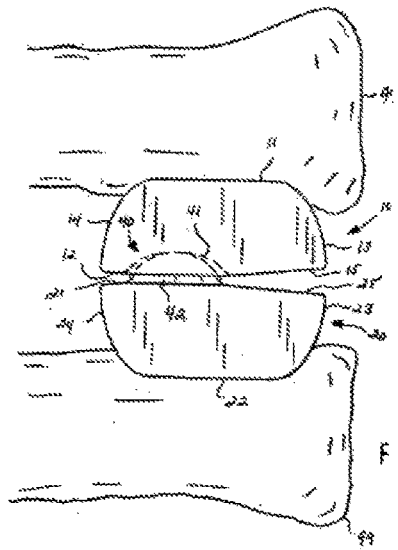

FIG. 5, plate 1/9, perspective view of the device corresponding to US Patent 20070233096 (prior art)

Figures 6, 7:
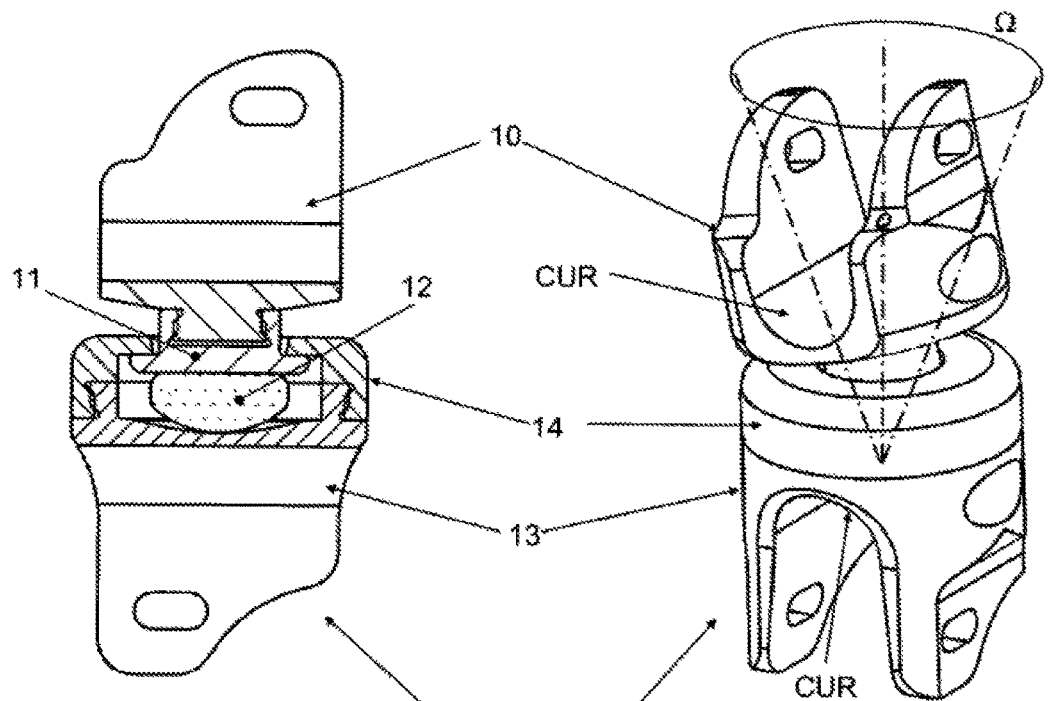
Figures 8, 9:
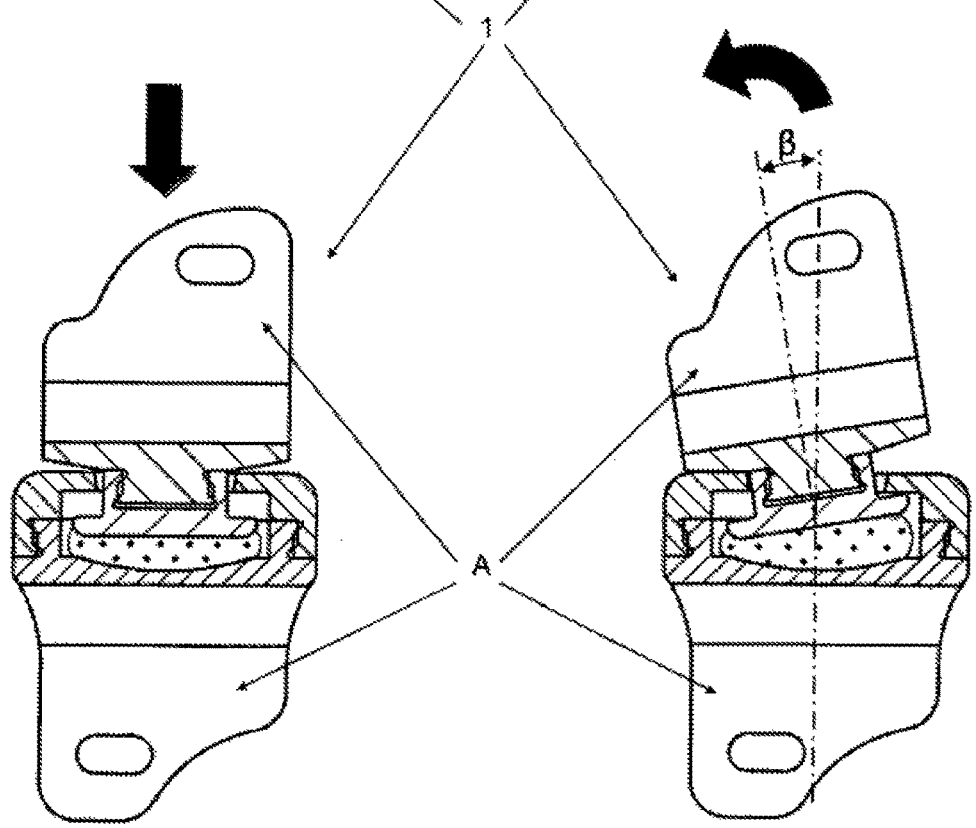
Figure 10:
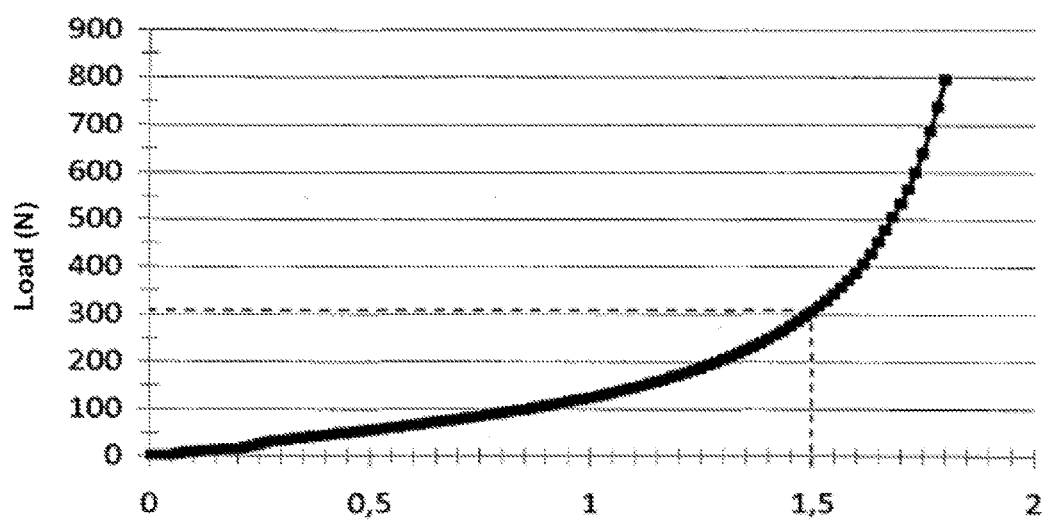
Figure 11:
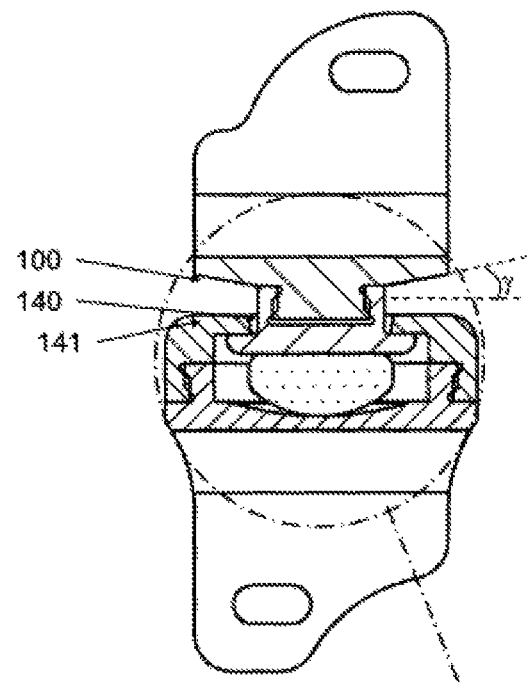
Figure 12:
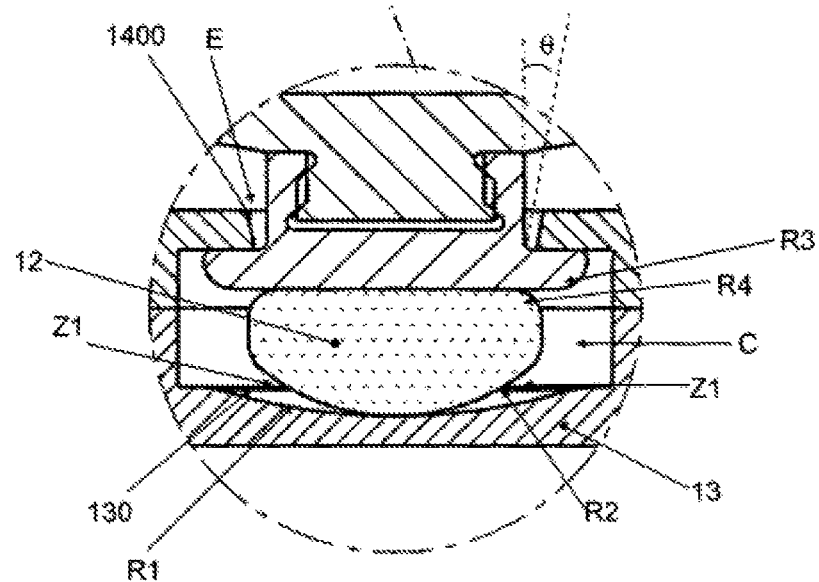
Figure 13:
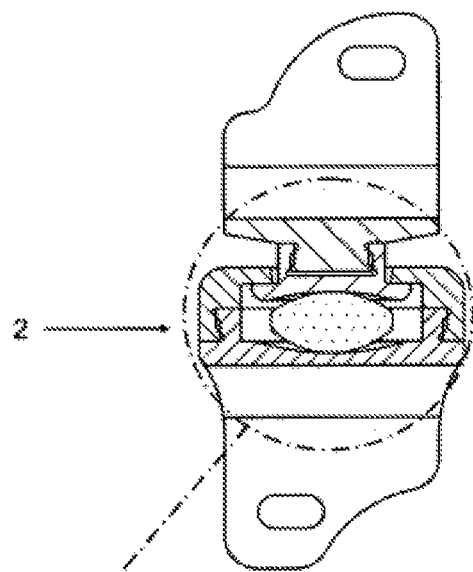
Figure 14:
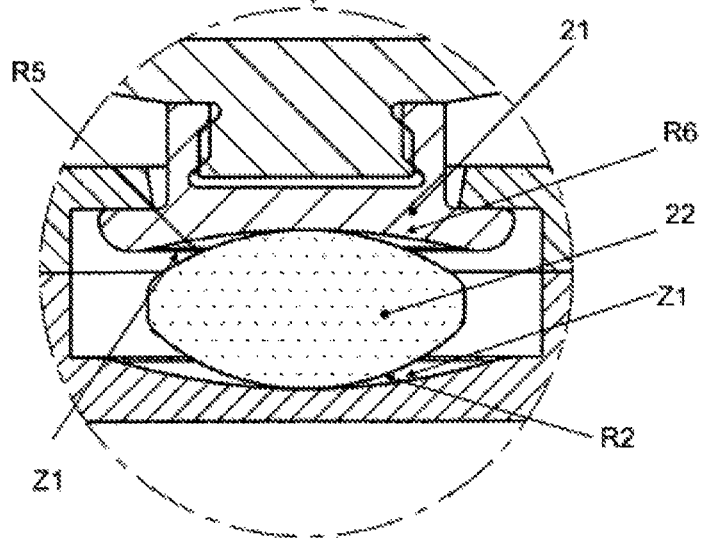
Figures 15, 16:
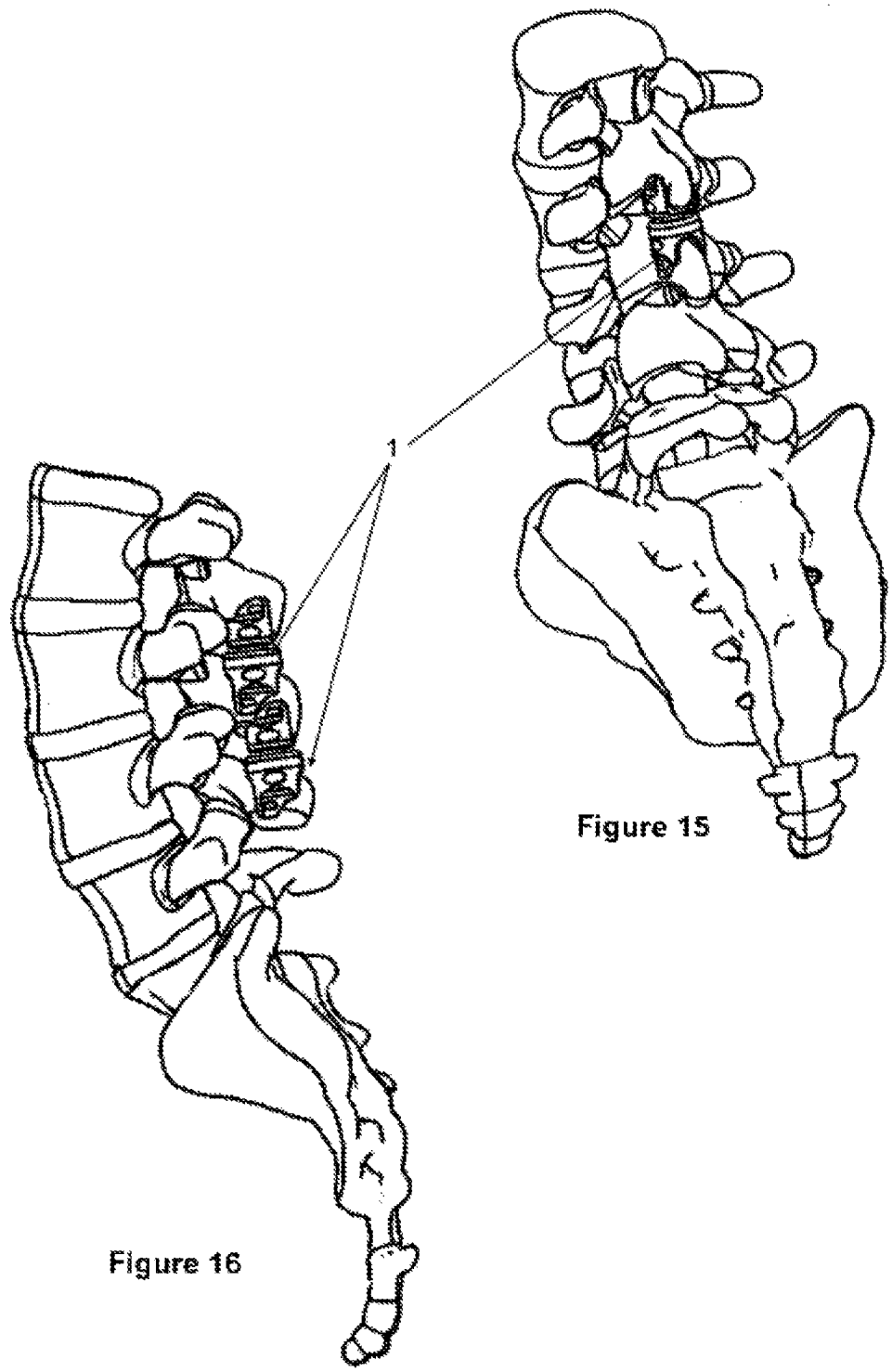
Figure 17:
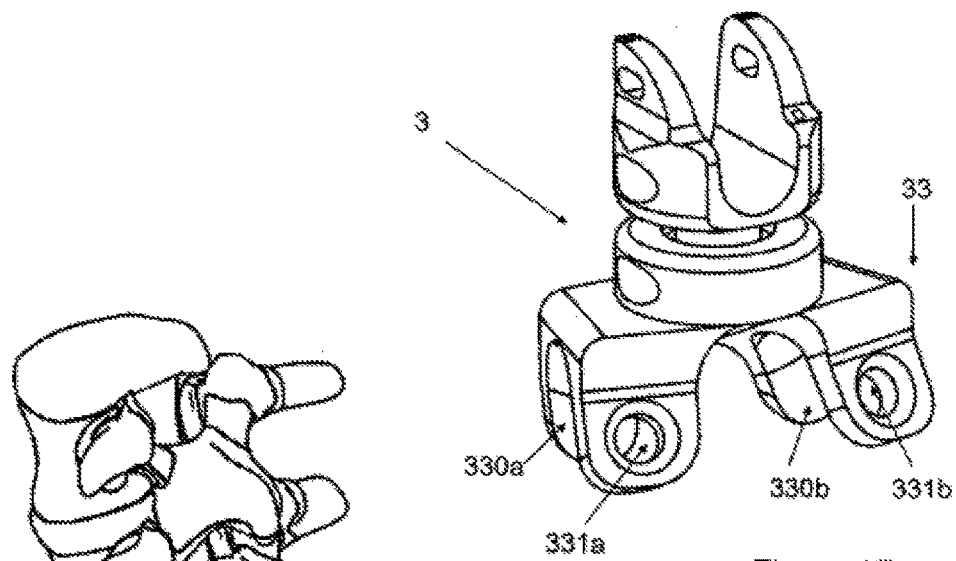
Figure 18:
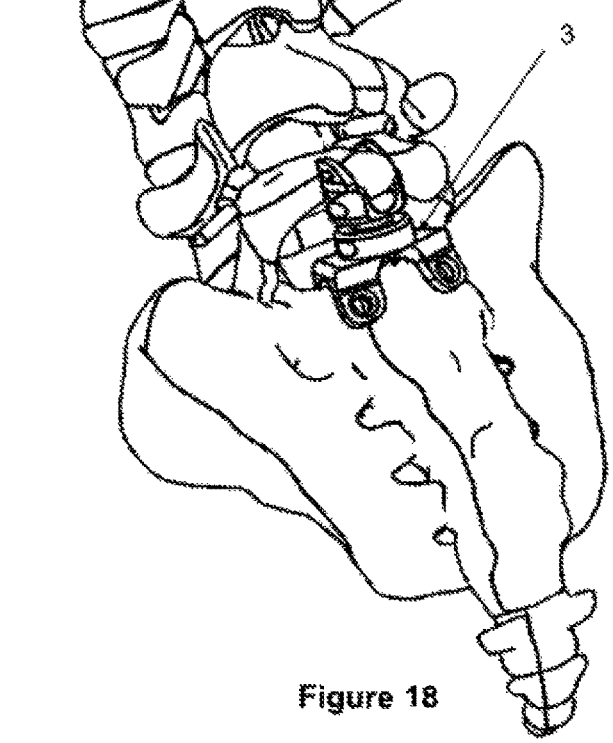
Figures 19, 20:
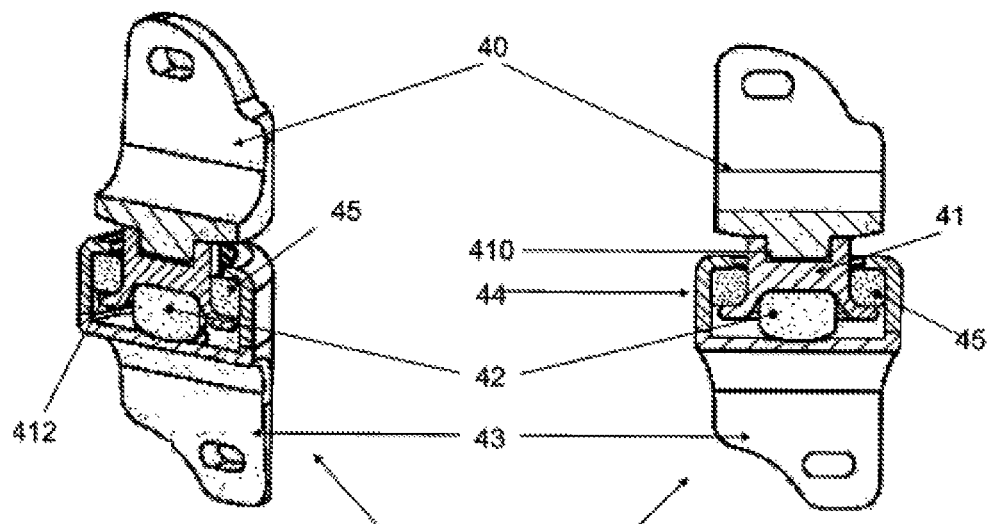
Figures 21, 22:
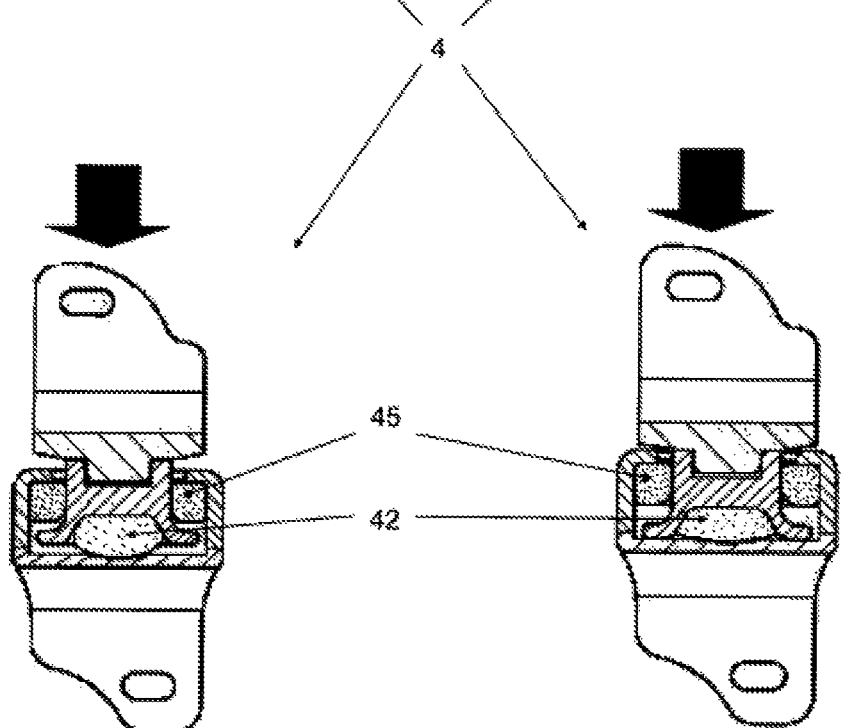
Figure 23:
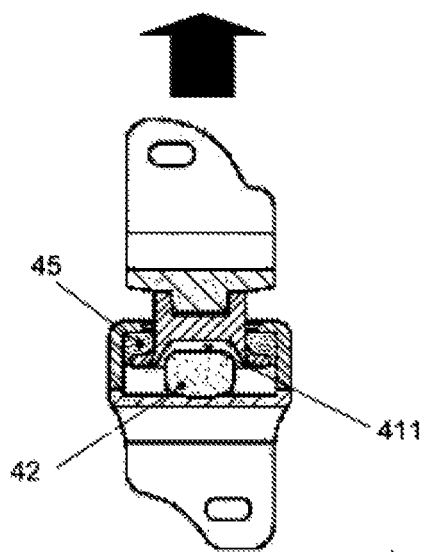
Figure 24:
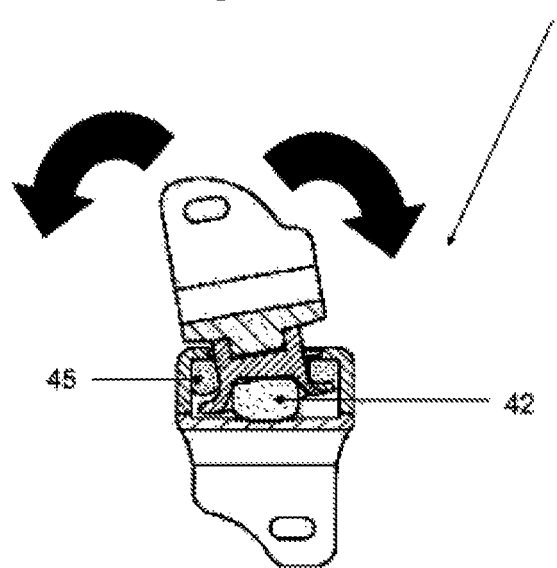

FIG. 6, plate 2/9, sectional view of the new device with the entirety of its means FIG. 7, plate 2/9, perspective view of the new device illustrating its multiaxial capabilities FIG. 8, plate 2/9, sectional view of the new device working in compression FIG. 9, plate 2/9, sectional view of the new device working in flexion FIG. 10, plate 3/9, characteristic in compression of the load applied on the device as a function of the displacement FIG. 11, plate 4/9, sectional view of the new device FIG. 12, plate 4/9, detail sectional view showing the differences between the radii of curvature of the rigid parts and the viscoelastic means FIG. 13, plate 5/9, sectional view of a first variant of the device with the entirety of its means FIG. 14, plate 5/9, detail sectional view of a first variant of the device showing the differences between the radii of curvature of the rigid parts and the viscoelastic means FIG. 15, plate 6/9, perspective view of the new device mounted on vertebrae FIG. 16, plate 6/9, profile view of two devices overlapping and mounted on vertebrae FIG. 17, plate 7/9, perspective view of a second variant of the device, with a lower hook adapted to the sacrum FIG. 18, plate 7/9, perspective view of this second variant mounted on the spine between the fifth lumbar vertebra and the sacrum FIG. 19, plate 8/9, isometric sectional view of a third variant of the device showing its rigid and viscoelastic means FIG. 20, plate 8/9, sectional view of this third variant showing its rigid and viscoelastic means at rest, without stress FIG. 21, plate 8/9, sectional view of this third variant in uniaxial compression FIG. 22, plate 8/9, sectional view of this third variant driven to a stop by maximum uniaxial compression FIG. 23, plate 9/9, sectional view of this third variant in uniaxial tension FIG. 24, plate 9/9, sectional view of this third variant in flexion.

Device 1, the object of the invention, comprises, in another embodiment, four rigid elements and one viscoelastic element (FIGS. 6 and 7):
 an upper hook 10,
 a piston 11, fixed to upper hook 10,
 a lower hook 13,
 a hollow cylindrical body 14, fixed on lower hook 13,
 a central viscoelastic element 12.

These upper and lower means 11 and 13 have the ability to move in multiaxial manner while being braced with a minimum of contact on a central means 12, which absorbs the deformations in compression and in flexion. Means 12 is disposed on a concave internal surface 130 of lower hook 13, which forms, together with hollow cylindrical body 14, a cavity C, in the interior of which piston 11 penetrates as far as contact with viscoelastic element 12. Device 1 is able to perform a movement analogous to that of a ball joint without suffering deterioration while integrating damping.

Device 1 permits all the multiaxial movements between the two hooks 10 and 13, by virtue of a combination of the entirety of the means, which are the two hooks 10 and 13, piston 11 and hollow cylindrical body 14 with viscoelastic element 12, which, lodged in cavity C, simultaneously acts as a damper and a ball joint, resuming its initial shape when the stresses cease.

Viscoelastic element 12, situated in cavity C placed between piston 11 and concave internal surface 130 of lower hook 13, has on its convex face a radius of curvature R2 different from the radius of curvature R1 of concave internal surface 130 (FIG. 12). If these radii of curvature were equivalent within the mounting clearances, strong adherence would be obtained, incompatible with good behavior of viscoelastic block 12. This latter would suffer, as in the prior art, elevated stress concentrations and large friction effects, which would lead to its premature destruction.

In the present invention, the values of radii R1 and R2 are calculated in order to obtain:
 automatic centering of viscoelastic element 12 in cavity C,
 permanent contact of viscoelastic element 12 with concave internal surface 130 of lower hook 13 and piston 11 throughout the duration of imposed deformations, regardless of their orientations,
 minimum wear of viscoelastic element 12.

These results are obtained by the maximum reduction of contact surfaces between viscoelastic element 12 and rigid means 11 and 13 without ever eliminating them and especially when device 1 is not being subjected to compression stress.

The differences of radii of curvature R1 and R2 creates an available space Z1 situated between concave internal surface 130 and viscoelastic element 12 (FIG. 12), wherein space Z1 is determined in such a manner that viscoelastic element 12 is able to be deformed freely regardless of the stress exerted by the piston.

These design characteristics make it possible to minimize the friction effects between viscoelastic element 12, piston 11 and concave surface 130 of hook 13, thus optimizing the useful life of device 1.

To obtain optimum functioning of device 1, it is necessary that radius R1 of viscoelastic element 12 be able to vary as a function of the mechanical load applied in compression on device 1 (FIG. 8). Radius R1 must be smaller than radius R2 when device 1 is not subjected to any stress (FIG. 12). In contrast, when device 1 is working at the maximum of its capacity, space Z1 tends toward 0, because it is completely filled by deformed viscoelastic element 12. In contrast, when R1=R2 (FIG. 8), the adherence of viscoelastic element 12 with hook 13 and piston 11 becomes maximum.

A peripheral space (E) situated between the body of piston (11) and the circular opening of orifice (140) of hollow cylindrical body (14) exists, which permits multiaxial ranges of movement of 1.5 mm that are controlled and, under load of upper hook (10) relative to lower hook (13), are limited to a maximum compression of viscoelastic element (12).

Piston 11, connected to upper hook 10, comprises a flat lower face with a transition radius R3 (FIG. 12), which is braced on viscoelastic element 12 without altering it, thus preventing contacts at acute angles, which has the effect of softening the said contacts during flexion movements on viscoelastic element 12, wherein this latter has a radius of curvature R4.

To obtain this result, radii R3 and R4 are constant and the contact surfaces of rigid means 11 and 13 with viscoelastic element 12 may be plane.

Upper hook 10 is able to pivot in multiaxial manner relative to lower hook 13 and to describe a solid angle $\Omega$ between one $100^{th}$ of $\pi$ and one $10^{th}$ of $\pi$ steradians. Its origin is situated at the intersection between the plane defined by the plane upper surface of viscoelastic element 12 and its center, by virtue of the deformation in flexion-compression of viscoelastic element 12 (FIG. 7) and also of the presence of:
 oblique frustoconical surface 1400 of orifice 140 of hollow cylindrical body 14 forming an angle $\theta$ with the vertical,
 the oblique lower face of upper hook 10, making an angle $\gamma$ with the horizontal,
 a free space E situated between the rim of piston 11 and the rim of orifice 140 of hollow cylindrical body 14, ranging between 0 and 3 mm.

Upper hook 10, which is movable relative to lower hook 13, has a range of movement $\beta$ between 0° and 10° and such that, if $\beta=0°$ (FIG. 9), the damping capacity of device 1 is maximum, whereas, if $\beta$ is maximum, its damping capacity becomes minimum; this function makes it possible to combine the damping and the mobility of device 1 between these extreme values.

The combination of oblique frustoconical surface 1400 of hollow cylindrical body 14 with space E and with viscoelastic element 12, which is compressed according to the mechanical characteristics defined by the curve of force (N)=f(displacement) (see FIG. 10), permits multiaxial displacements that are controlled and, under load of upper hook 10 relative to lower hook 13, up to a maximum compression equal to 1.5 mm. Beyond this value, hook 10, which has a surface 100 at its end, becomes stopped against surface 141 of cylindrical body 14. This stop secures device 1 in the intervertebral space and guarantees good functioning of device 1, thus preventing any incident and deterioration during overloads applied to viscoelastic means 12. In addition, the characteristic in compression of the load applied on device 1 as a function of the displacement (FIG. 10) exhibits a quasi-linear mode of deformation up to approximately 1.5 mm of compression, which corresponds to an applied force close to 310 N. This value of force corresponding to 1.5 mm of displacement is deliberately calibrated to be slightly smaller than 339 N, the value of rupture of the spinal apophyses on which device 1 is fixed, in order that the said device will not damage the vertebrae in case of large mechanical stresses.

This device 1 makes it possible to restore the biomechanics of a healthy intervertebral joint.

The shapes of the two upper 10 and lower 13 hooks are defined in such a way that each device 1, considered separately, is able to overlap with its neighbor. Each hook 10 and 13 has two wings A capable of interlocking in complementary manner in another neighboring wing A (FIGS. 8 and 9), positioned symmetrically relative to the preceding already implanted wing, thus making it possible to position devices 1 side-by-side without causing them to obstruct or interfere with one another while keeping them in good alignment on the spine. This makes it possible to consolidate several intervertebral levels with good alignment and without offset (FIG. 16).

Wings A are an integral part of each hook and become embraced between the spinal apophyses and, because of their specific shape, conform to their contour, thus stabilizing viscoelastic means 12 in its lodging while preventing any translation relative to its central position of normal functioning. The internal part situated between the wings has a curvilinear shape CUR (FIG. 7), which conforms to the shape of the spinal apophysis and prevents any slippage (FIG. 15).

Device 1 has an assembly prestress, which applies slight compression to viscoelastic means 12, which, by reaction, is able to press piston 11 against the internal wall of cylindrical body 14.

A first variant of device 1 (FIGS. 13 and 14), denoted device 2, is provided with a biconvex viscoelastic element 22 having radii of curvature R2 and R5, which may be identical or different, as well as a piston 21 having a radius of curvature R6 greater than the radius of curvature R5 of viscoelastic element 22, in such a manner as to generate a free space Z2 permitting free deformation, without excessive friction with piston 21, of viscoelastic element 22 during mechanical stresses. The biconvex geometry, resembling an optical lens, of viscoelastic element 22, combined with the concavity of piston 21, favor the movements of ball-joint type of device 2 while minimizing the risks of wear of the pieces by friction.

In another embodiment (FIG. 17), device 3, which is a variant of device 1, has a lower hook 33 that replaces lower hook 13 of the preceding version. Lower hook 33 has a shape that resembles that of a saddle for a horse, allowing it to adapt to the shape of the sacrum while guaranteeing perfect stability.

This hook 33 has two lateral stirrups 330a and 330b provided with orifices 331a and 331b, which permit quasi-perfect nesting on the sacrum and solid fixation by anchoring means, such as small screws, which pass through the said orifices and partially the bone of the sacrum.

This shape of device 3 assures very good stability at the level of the intervertebral joint with the sacrum.

A third alternative embodiment of device 1, denoted device 4, comprises four rigid elements and two viscoelastic elements (FIG. 19):
an upper hook 40,
a piston 41, fixed to upper hook 40,
a lower hook 43,
a hollow cylindrical body 44, fixed on lower hook 43,
a central viscoelastic element 42.

The geometry of the means of this third variant that are part of the first embodiment was modified to integrate a supplementary means, i.e. a viscoelastic ring 45, which introduces new functions.

Piston 41 has a fixation 410, which permits the connection with upper hook 40. It has geometry different from that of piston 11, because it has a cavity 411 that functions as lodging of central viscoelastic element 42 as well as a crown 412, on which viscoelastic ring 45, the new means of device 4, rests. This makes it possible to include viscoelastic ring 45 together with damper block 42 in a restricted space defined by the interior of hollow cylindrical body 44.

The combination of all of these means and the integration of viscoelastic ring 45 permits damping of mechanical stresses, especially in tension, which is not possible with the preceding variants of the invention. Crown 412 of piston 41 acts as a limiter of loads applied to viscoelastic element 42 and functions as safety stop during extreme mechanical forces acting on device 4 in compression.

Viscoelastic ring 45 is lodged with minimum clearance between the internal walls of hollow cylindrical body 44 and the upper part of piston 41, which makes it possible, by virtue of this minimum clearance, to obtain instantaneously an elastic restoring force during displacements of upper hook 40 in flexion, tending to return it to its neutral position. The integration of viscoelastic ring 45 makes it possible to damp the mechanical stresses in traction and flexion and to increase the amplitude of displacement of device 4 relative to the preceding variants while preserving the damping in compression.

Devices 1, 2, 3 and 4 make it possible to restore the mobility and damping of the intervertebral joints of the sacro-lumbar column.

The invention claimed is:

1. A dynamic intervertebral stabilization device comprising:
an upper hook,
a lower hook,
a hollow cylindrical body, and
a central viscoelastic element,
wherein the upper hook integrates a piston, which is braced with a minimum of contact on the central viscoelastic element, which permits the upper and lower hooks to be moved in a multiaxial manner within a solid angle $\Omega$ while absorbing deformations in compression and in flexion by virtue of the damping produced by the central viscoelastic element, wherein the lower hook forms together with the hollow cylindrical body a cavity into which said piston penetrates as far as contact and said lower hook has a concave internal surface in said cavity,
wherein the central viscoelastic element has a convex face with a radius of curvature R2 smaller than a radius of curvature R1 of the concave internal surface, thus permitting it to be positioned at a center of the concave internal surface, which leads to a reduction of contact surfaces, and
wherein difference of the radii of curvature R1 and R2 creates an available space situated between the concave internal surface and the central viscoelastic element,
wherein the radius R2 of the central viscoelastic element is able to vary as a function of a mechanical load applied in compression on the dynamic intervertebral stabilization device, which has a consequence that, in a first position, the radius R2 is smaller than the radius R1 when the dynamic intervertebral stabilization device is not subjected to any stress and, in a second position, when R1 is equal to R2, the dynamic intervertebral stabilization device is working at the maximum of its capacity, the available space, tending toward 0, is then completely filled by the central viscoelastic element, which is capable of such a deformation.

2. The dynamic intervertebral stabilization device according to claim 1, wherein said device further comprises:
a viscoelastic ring, and wherein the hollow cylindrical body is fixed on the lower hook.

3. The dynamic intervertebral stabilization device according to claim 2 wherein the piston comprises:
   a cavity that functions as lodging of the central viscoelastic element, and
   a crown, on which the viscoelastic ring rests,
   such that the viscoelastic ring together with the viscoelastic element are located in a restricted space defined by an interior of the hollow cylindrical body.

4. The dynamic intervertebral stabilization device according claim 3, wherein the crown of the piston acts as a limiter of loads applied to the viscoelastic element and functions as a safety stop during extreme mechanical forces acting on the dynamic intervertebral stabilization device in compression.

5. The dynamic intervertebral stabilization device according to claim 2 wherein the viscoelastic ring is lodged with a minimum clearance between internal walls of the hollow cylindrical body and an upper part of the piston, which makes it possible to obtain instantaneously an elastic restoring force during displacements of the upper hook in flexion, tending to return it to its neutral position.

6. The dynamic intervertebral stabilization device according to claim 2, wherein the viscoelastic ring makes it possible to dampen the mechanical stresses in traction and flexion and to increase an amplitude of displacement of the dynamic intervertebral stabilization device while preserving the damping in compression.

7. The dynamic intervertebral stabilization device according to claim 1, wherein the central viscoelastic element is braced on a concave internal surface of the lower hook, which forms, together with the hollow cylindrical body, a cavity in the interior of which the piston penetrates as far as contact with the central viscoelastic element, thus permitting the dynamic intervertebral stabilization device to be moved in a manner of a bail joint.

8. The dynamic intervertebral stabilization device according to claim 7, wherein a peripheral space situated between a body of the piston and a circular opening of an orifice of the hollow cylindrical body exists, which permits multiaxial ranges of movement that are controlled and, under load of the upper hook relative to the lower hook, are limited to a maximum compression of the central viscoelastic element equal to 1.5 mm, an end of the upper hook in this case becoming stopped against a surface of the hollow cylindrical body, wherein this stop secures functioning of the dynamic intervertebral stabilization device in intervertebral space.

9. The dynamic intervertebral stabilization device according to claim 1, wherein the available space is such that the central viscoelastic element is able to be deformed freely regardless of stress exerted by the piston.

10. The dynamic intervertebral stabilization device according to claim 1, wherein the upper hook has two neighboring upper wings and the lower hook has two neighboring lower wings, said two neighboring upper wings being capable of interlocking with two neighboring lower wings of a first another dynamic intervertebral stabilization device, and said two neighboring lower wings being capable of interlocking with two neighboring upper wings of a second another dynamic intervertebral stabilization device such that said dynamic intervertebral stabilization device the first and second another dynamic intervertebral stabilization devices are positioned side-by-side without causing them to interfere with one another while keeping an alignment of the devices on the spine.

11. The dynamic intervertebral stabilization device according to claim 1, further comprising a biconvex viscoelastic element having radii of curvature (R2) and (R5) as well as a piston having a radius of curvature (R6) greater than the radius of curvature (R5), in such a manner that a free space is generated, permitting free deformation, without excessive friction with the piston, of the biconvex viscoelastic element during mechanical stresses.

12. The dynamic intervertebral stabilization device according to claim 1 wherein the lower hook has a saddle shape in contact with a sacrum, allowing the lower hook to adapt to the shape of the sacrum while ensuring stability, wherein the hook has two lateral stirrups with orifices which permit quasi-perfect nesting with the sacrum and solid fixation by anchoring.

13. The dynamic intervertebral stabilization device according to claim 1, wherein the hollow cylindrical body has a circular orifice, and said device comprises a free peripheral space E situated between the piston and the circular orifice which permits multiaxial ranges of movement of 1.5 mm.

14. The dynamic intervertebral stabilization device according to claim 1, wherein the hollow cylindrical body has a circular orifice, and said device comprises a free space E situated between the piston and the circular orifice ranging between 0 and 3 mm.

15. A set of dynamic intervertebral stabilization devices comprising:
   a main dynamic intervertebral stabilization device according to claim 1,
   a first dynamic intervertebral stabilization device comprising;
   a first upper hook having two first neighboring upper wings,
   a first lower hook having two first neighboring lower wings,
   a first hollow cylindrical body, and
   a first central viscoelastic element,
   wherein the first upper hook integrates a piston, which is braced with a minimum of contact on the central viscoelastic element, which permits the first upper and the first lower hooks to be moved in a multiaxial manner within a solid angle $\Omega$ while absorbing deformations in compression and in flexion by virtue of the damping produced by the first central viscoelastic element,
   a second dynamic intervertebral stabilization device comprising:
   a second upper hook having two second neighboring upper wings,
   a second lower hook having two second neighboring lower wings,
   a second hollow cylindrical body, and
   a second central viscoelastic element,
   wherein the second upper hook integrates a piston, which is braced with a minimum of contact on the second central viscoelastic element, which permits the second upper and the second lower hooks to be moved in a multiaxial manner within a solid angle $\Omega$ while absorbing deformations in compression and in flexion by virtue of the damping produced by the second central viscoelastic element,
   and wherein
   the upper hook of the main dynamic intervertebral stabilization device has two neighboring upper wings and the lower hook of the main dynamic intervertebral stabilization device has two neighboring lower wings,
   and wherein
   said two neighboring upper wings being capable of interlocking with two first neighboring lower wings of the first another dynamic intervertebral stabilization device, and said two neighboring lower wings being capable of interlocking with two second neighboring upper wings of the second another dynamic intervertebral stabilization device such that said main, first and second dynamic intervertebral stabilization devices are positioned side-by-side without causing them to interfere with one another while keeping an alignment of the devices on the spine.

* * * * *